(12) United States Patent
Boedeker et al.

(10) Patent No.: US 9,848,847 B2
(45) Date of Patent: Dec. 26, 2017

(54) USING DETECTABILITY INDEX TO DETERMINE X-RAY TUBE CURRENT

(71) Applicant: TOSHIBA MEDICAL SYSTEMS CORPORATION, Otawara-shi (JP)

(72) Inventors: Kirsten Boedeker, Los Angeles, CA (US); Satoru Nakanishi, Arlington Heights, IL (US)

(73) Assignee: Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 14/680,867

(22) Filed: Apr. 7, 2015

(65) Prior Publication Data

US 2016/0296196 A1  Oct. 13, 2016

(51) Int. Cl.
*A61B 6/03* (2006.01)
*A61B 6/00* (2006.01)

(52) U.S. Cl.
CPC .............. *A61B 6/544* (2013.01); *A61B 6/032* (2013.01); *A61B 6/5205* (2013.01); *A61B 6/545* (2013.01); *A61B 6/582* (2013.01)

(58) Field of Classification Search
CPC .......... A61B 6/032; A61B 6/54; A61B 6/542; A61B 6/544; A61B 6/5205; A61B 6/5217; A61B 6/5258; A61B 6/467
See application file for complete search history.

(56) References Cited

U.S. PATENT DOCUMENTS

| | | | | |
|---|---|---|---|---|
| 5,590,164 A | * | 12/1996 | Kawai | A61B 6/032 378/19 |
| 5,825,846 A | * | 10/1998 | Aach | G06T 5/20 378/62 |
| 2003/0097062 A1 | * | 5/2003 | Toth | A61B 6/032 600/425 |
| 2004/0202277 A1 | * | 10/2004 | Okumura | A61B 6/032 378/16 |
| 2007/0081630 A1 | * | 4/2007 | Evron | A61B 5/02007 378/108 |
| 2009/0122952 A1 | * | 5/2009 | Nishide | A61B 6/032 378/4 |
| 2009/0141854 A1 | * | 6/2009 | Hirokawa | A61B 6/032 378/4 |
| 2012/0140894 A1 | * | 6/2012 | Feuerlein | A61B 6/032 378/112 |
| 2014/0072108 A1 | * | 3/2014 | Rohler | A61B 6/482 378/207 |

FOREIGN PATENT DOCUMENTS

| | | |
|---|---|---|
| JP | 2003-190139 A | 7/2003 |
| JP | 2004-305527 A | 11/2004 |
| JP | 2009-112627 A | 5/2009 |
| JP | 2010-193940 A | 9/2010 |
| JP | 2010193940 A * | 9/2010 |

\* cited by examiner

*Primary Examiner* — David E Smith
(74) *Attorney, Agent, or Firm* — Oblon, McClelland, Maier & Neustadt, L.L.P.

(57) ABSTRACT

A computed tomography (CT) image apparatus includes an X-ray source to emit X-rays; and processing circuitry configured to receive a desired detectability index set by a user, the desired detectability index determining for a desired image quality of a CT scan of an object; determine an X-ray tube current that will result in the desired detectability index set by the user; and cause the X-ray source to perform a scan of the object using the determined tube current.

6 Claims, 7 Drawing Sheets d' =6.0 d' =5.6 d' =5.2

USING DETECTABILITY INDEX TO DETERMINE X-RAY TUBE CURRENT

FIELD

The exemplary embodiments described herein relate to computed tomography (CT) systems.

BACKGROUND

CT systems and methods are widely used, particularly for medical imaging and diagnosis. CT systems generally create images of one or more sectional slices through a subject's body. A radiation source, such as an X-ray tube, irradiates the body from one side thereof. A collimator, generally adjacent to the X-ray source, limits the angular extent of the X-ray beam, so that radiation impinging on the body is substantially confined to a planar region defining a cross-sectional slice of the body. At least one detector (and generally many more than one detector) on the opposite side of the body receives radiation transmitted through the body substantially in the plane of the slice. The attenuation of the radiation that has passed through the body is measured by processing electrical signals received from the detector.

Typically, in commonly-used third- and fourth-generation CT scanners, the X-ray source (or multiple sources) is mounted on a gantry, which revolves about a long axis of the body. In third-generation scanners, the detectors are likewise mounted on the gantry, opposite the X-ray source, while in fourth-generation scanners, the detectors are arranged in a fixed ring around the body. Either the gantry translates in a direction parallel to the long axis, or the body is translated relative to the gantry. By appropriately rotating the gantry and translating the gantry or the subject, a plurality of views may be acquired, each such view comprising attenuation measurements made at a different angular and/or axial position of the source. Commonly, the combination of translation and rotation of the gantry relative to the body is such that the X-ray source traverses a spiral or helical trajectory with respect to the body. The multiple views are then used to reconstruct a CT image showing the internal structure of the slice or of multiple such slices, using conventional methods. The lateral resolution of the CT image, or specifically, the thickness of the slices making up the image, is generally determined by the angular extent of the radiation beam or of the individual detectors, whichever is smaller.

Traditionally, adaptive noise reduction techniques are used to remove the noise. However, those techniques generate a non-linear relationship between the image noise and the X-ray tube current.

BRIEF DESCRIPTION OF THE DRAWINGS

A more complete appreciation of the teachings of this disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

In one embodiment, there is provided a computed tomography (CT) imaging apparatus, including: (1) an X-ray source to emit X-rays; and (2) processing circuitry configured to receive a desired detectability index set by a user, the desired detectability index determining for a desired image quality of a CT scan of an object; determine an X-ray tube current that will result in the desired detectability index set by the user; and cause the X-ray source to perform a scan of the object using the determined tube current.

In another embodiment, there is provided a computed tomography (CT) imaging method for a CT apparatus that includes an X-ray source configured to emit X-rays, including: (1) receiving a desired detectability index set by a user for a desired image quality of a CT scan of an object; (2) determining an X-ray tube current that will result in the desired detectability index set by the user; and (3) causing the X-ray source to perform a scan of the object using the determined tube current.

In another embodiment, there is provided a non-transitory computer-readable medium storing executable instructions, which when executed by processing circuitry of a CT apparatus that includes an X-ray source configured to emit X-rays, cause the processing circuitry to execute a method including: (1) receiving a desired detectability index set by a user for a desired image quality of a CT scan of an object; (2) determining an X-ray tube current that will result in the desired detectability index set by the user; and (3) causing the X-ray source to perform a scan of the object using the determined tube current.

Figure 1:
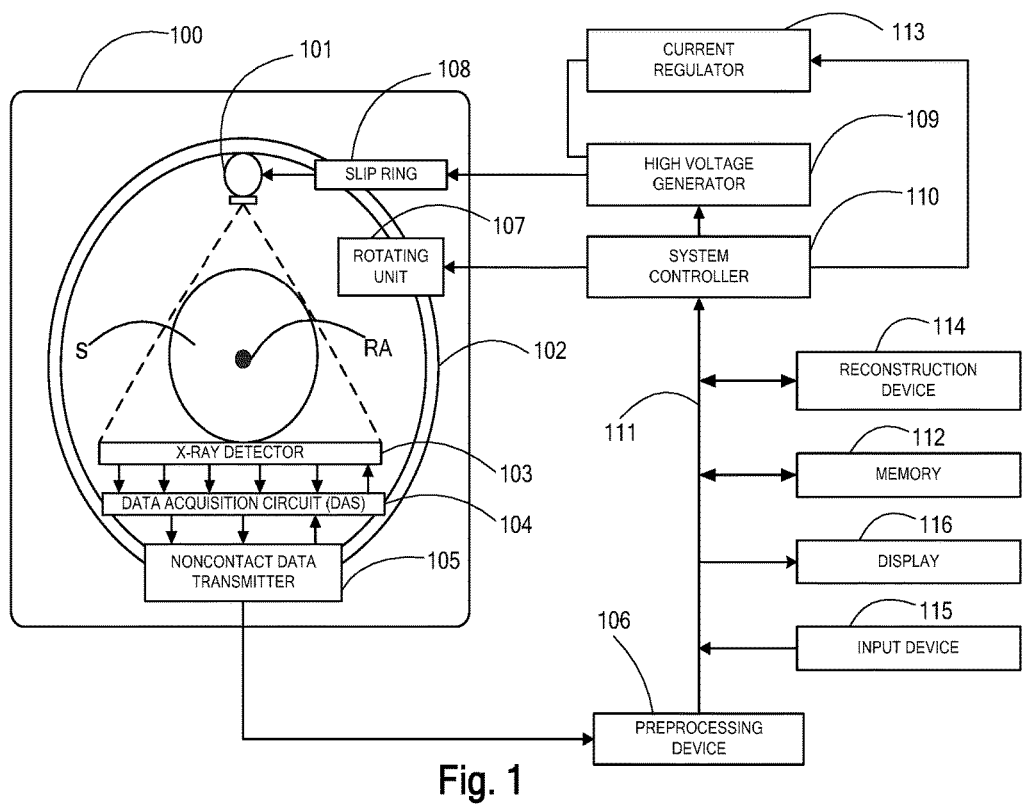
FIG. 1 illustrate exemplary CT scanner systems.

FIG. 1 illustrates an implementation of the radiography gantry in a CT apparatus or scanner. As shown in FIG. 1, the radiography gantry 100 is illustrated from a side view and further includes an X-ray tube 101, an annular frame 102, and a multi-row or two-dimensional array type X-ray detector 103. The X-ray tube 101 and X-ray detector 103 are diametrically mounted across a subject S on the annular frame 102, which is rotatably supported around a rotation axis RA. A rotating unit 107 rotates the annular frame 102 at a high speed, such as 0.4 sec/rotation, while the subject S is being moved along the axis RA into or out of the illustrated page.

The multi-slice X-ray CT apparatus further includes a high voltage generator 109 that generates a tube voltage applied to the X-ray tube 101 through a slip ring 108 so that the X-ray tube 101 generates X-rays. The X-rays are emitted towards the subject S, whose cross sectional area is represented by a circle. The X-ray detector 103 is located at an opposite side from the X-ray tube 101 across the subject S for detecting the emitted X-rays that have transmitted through the subject S. The X-ray detector 103 further includes individual detector elements or units.

With continued reference to FIG. 1, the CT apparatus further includes other devices for processing the detected signals from X-ray detector 103. A data acquisition circuit or a Data Acquisition System (DAS) 104 converts a signal output from the X-ray detector 103 for each channel into a voltage signal, amplifies the signal, and further converts the signal into a digital signal. The X-ray detector 103 and the DAS 104 are configured to handle a predetermined total number of projections per rotation (TPPR). Examples of TPPRs include, but are not limited to 900 TPPR, 900-1800 TPPR, and 900-3600 TPPR.

The above-described data is sent to a preprocessing device 106, which is housed in a console outside the radiography gantry 100 through a non-contact data transmitter 105. The preprocessing device 106 performs certain corrections, such as sensitivity correction on the raw data. A memory 112 stores the resultant data, which is also called projection data at a stage immediately before reconstruction processing. The memory 112 is connected to a system controller 110 through a data/control bus 111, together with a reconstruction device 214, input device 115, and display 116.

The detectors are rotated and/or fixed with respect to the patient among various generations of the CT scanner systems. The above-described CT system is an example of a combined third-generation geometry and fourth-generation geometry system. In the third-generation system, the X-ray tube 101 and the X-ray detector 103 are diametrically mounted on the annular frame 102 and are rotated around the subject S as the annular frame 102 is rotated about the rotation axis RA. In the fourth-generation geometry system, the detectors are fixedly placed around the patient and an X-ray tube rotates around the patient.

In an alternative embodiment, the radiography gantry 100 has multiple detectors arranged on the annular frame 102, which is supported by a C-arm and a stand.

Various indexes that represent image noise standard variation have been used to determine a X-ray tube current (mA) for automatic exposure control (AEC). Patients come in a wide array of sizes, ranging from newborns weighing a few kilograms, to small adults of approximately 50 kg, to large adults of 120 kg (or greater, in the case of obese patients). Usually, a larger index value indicates a noisy image and worse image quality, while a smaller index indicates a less noisy image and better image quality. Default indices range from 7.5 HU to 20.0 HU, for example. In order to have a smaller image-noise standard deviation, the CT system increases the X-ray tube current when the index is small, and decreases the X-ray tube current when the index is large. Moreover, the X-ray tube current is related to the size of a patient. For a large patient and a large index, the CT system needs to use more X-ray current to guarantee a specified image noise compared to a small patient and a small index.

Thus, the disclosed embodiments are directed to systems that modulate the baseline current and the z-tube current.

Figure 2A:
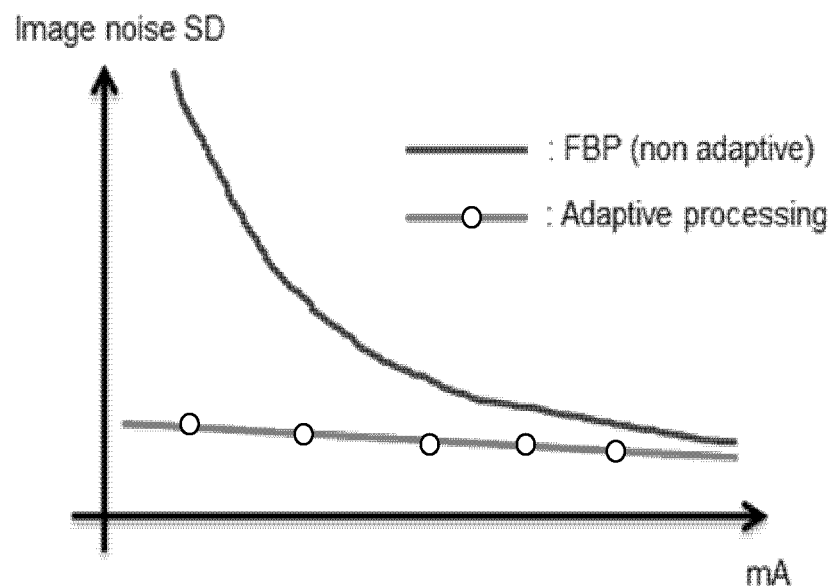
FIG. 2A illustrates an exemplary graph of image noise standard deviation vs. X-ray tube current.
Figure 2B:
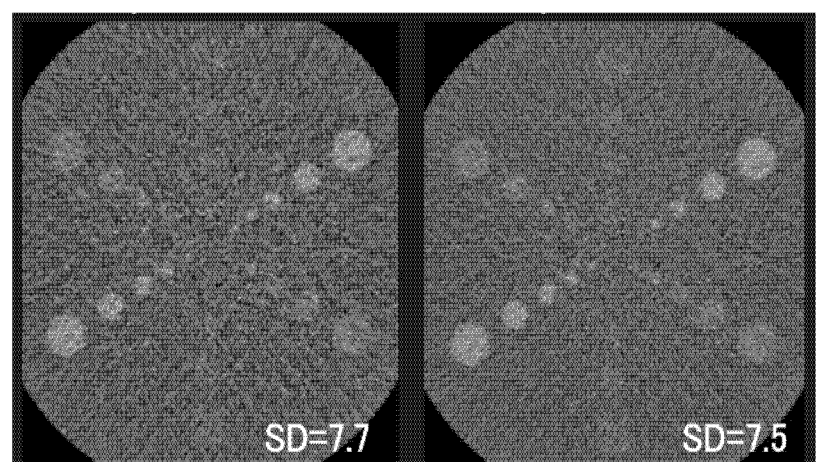
FIG. 2B illustrates an exemplary graph of image noise standard deviation vs. noise grain.

Adaptive noise reduction techniques, such as an edge-preserving image filter, a hybrid image filter, and a true image filter generate a non-linear relationship between the image noise and the X-ray tube current. For example, in FIG. 2A, an image noise standard deviation (SD) for adaptive processing is not changed proportionally with the X-ray tube current "mA". Moreover, as shown in FIG. 3B, images with the similar SDs (7.7 and 7.5) have different noise-grain sizes.

Figure 3A:
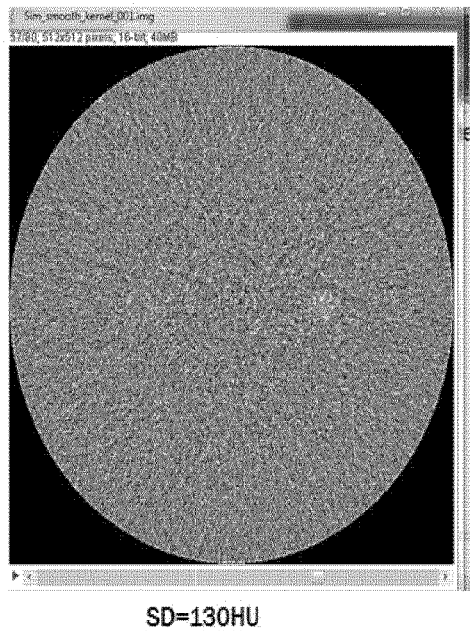
FIGS. 3A-B illustrate exemplary graphs of images with standard deviations (SD) of 130 HU, and 131.6 HU, respectively.
Figure 3B:
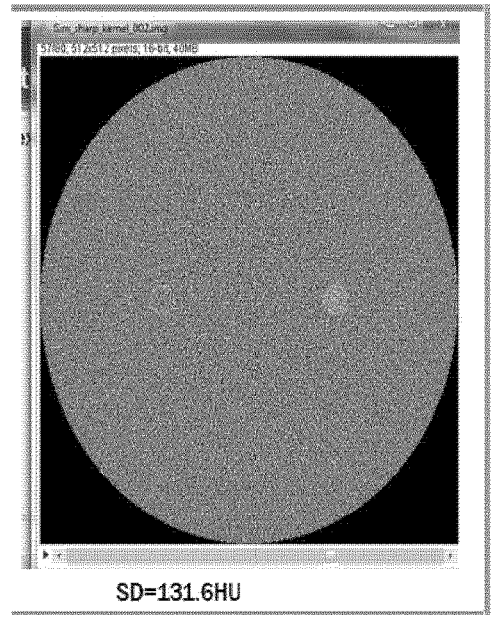

FIGS. 3A and 3B illustrate the effects on the detectability of noise textures with the same image noise SDs. The reconstruction kernel is defined as an image processing filter applied to the raw data to yield a final scan image. The reconstruction kernel is an important component that affects the image quality. Generally speaking, there is a tradeoff between the spatial resolution and the noise for each kernel. A smooth kernel generates images with lower noise, but with reduced spatial resolution. A sharp kernel generates images with higher spatial resolution, but increases the image noise.

In the example shown in FIGS. 3A and 3B, a 20 cm-diameter water phantom with a 15 mm, 100 Hounsfield unit (HU) rod, and a 100 HU ring (outer radius 15 mm and inner radius 7.5 mm) was used to generate datasets. Two datasets were acquired at 120 kV with a 240-degree field-of-view (FOV), an 80×0.5 mm axial acquisition, with 900 views, using an AqOne protocol. The first dataset was simulated with a smooth reconstruction kernel (FC 13), while the second dataset was simulated with a sharp reconstruction kernel. The X-ray tube current was adjusted to keep the same SDs for both datasets.

Figure 3C:
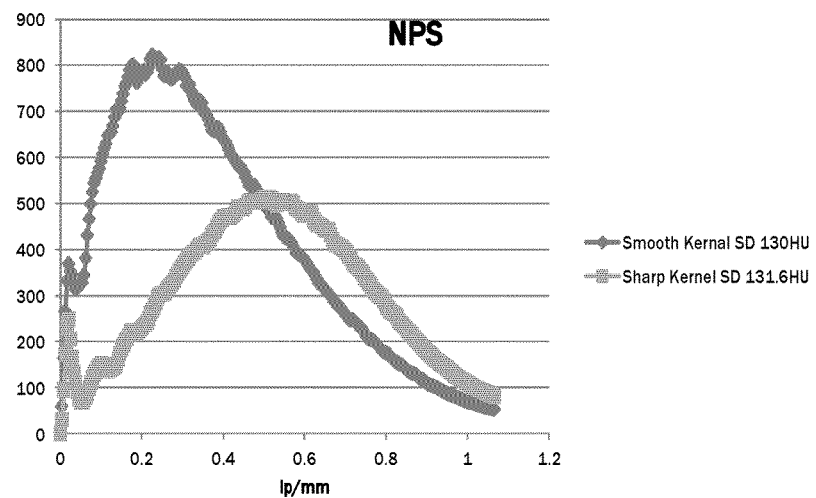
FIG. 3C illustrates an exemplary graph of noise power spectrums (NPS) of the two images in FIGS. 3A-B.

FIG. 3C is an exemplary graph of the noise power spectra (NPS) for the two simulated images. The Fourier transform is based on the assumption that the system is linear and deterministic. A system is deterministic if, when presented with two identical input signals, it produces two identical output signals. However, random noise occurs in most systems, causing small fluctuations in the output signal. Thus, the NPS can be described as the variance in image intensity over the spatial frequencies in an image, or as the variance of a given spatial frequency in repeated measurements of that specific frequency. In FIG. 3C, for the dataset of the smooth reconstruction kernel with a SD of 130 HU, the NPS is significantly different from the dataset of the sharp reconstruction kernel with a SD of 131.6 HU. Thus, image quality requires other indices beside the image noise SD, and another index that includes the noise grain size is important to search for an appropriate X-ray tube current to maintain diagnostic value.

Figure 4:
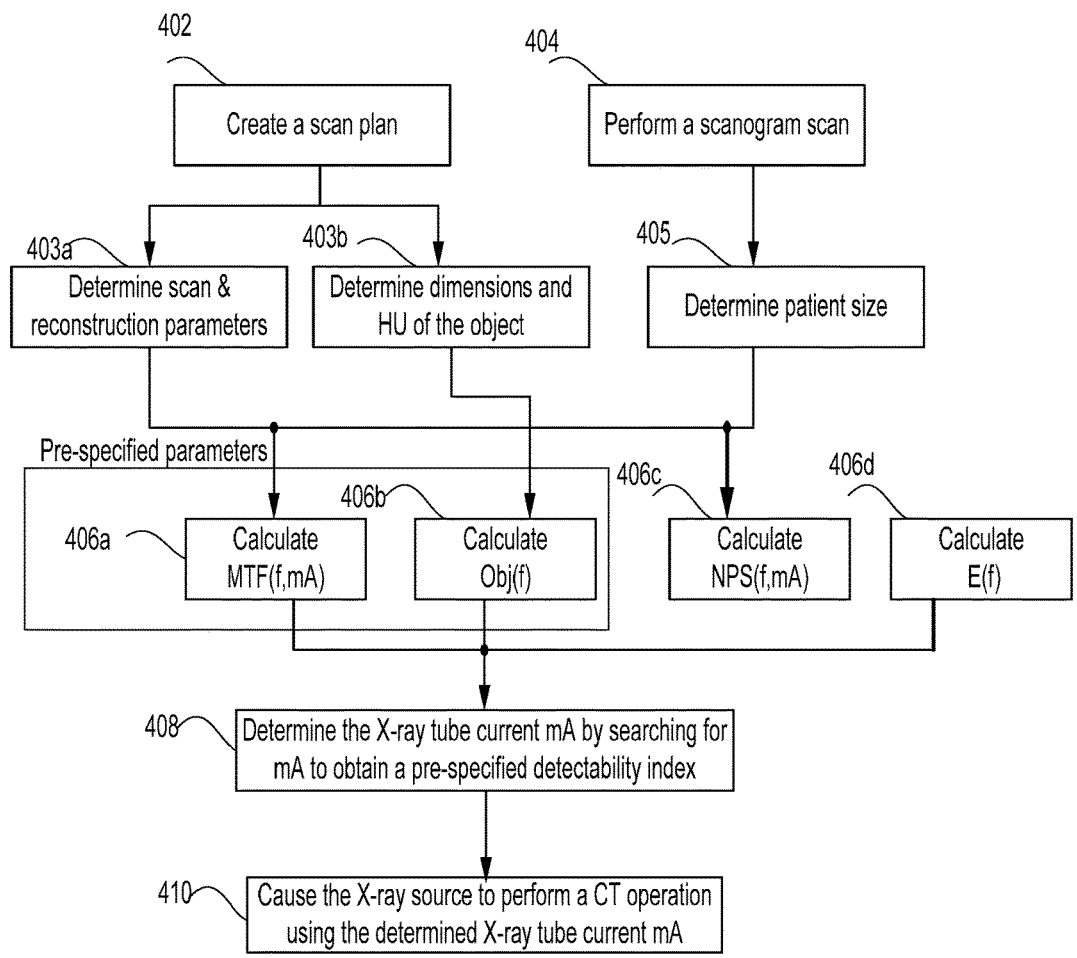
FIG. 4 illustrates a method to determine the X-ray tube current, by way of a flowchart.

Referring to FIG. 4, a flowchart 400 describes a method for determining a proper X-ray tube current mA given a desired detectability index.

In step 402, a user-specified scan plan is created.

In step 403a, the processing circuitry determines a set of scan and reconstruction parameters based on the user-specific scan plan created in step 402. The scan plan determines the range of X-ray exposure along the length of the patient and, based on the scan type selected, a set of scan parameters (such as kVp, pitch, collimation, and FOV) and reconstruction parameters (such as reconstruction kernel and post-processing filters) are automatically determined by the system. If desired, these pre-loaded acquisition and reconstruction parameters can be adjusted by the user.

In step 403b, the processing circuitry determines the dimensions of the patient (or object to be scanned) as well as the patient's or object's attenuation, expressed in HU, from the user-specific scan plan created in step 402. In step 404, the processing circuitry causes the CT scanner to perform a scanogram scan to obtain a scanogram.

In step 405, the processing circuitry determines anterior-posterior (i.e., length) and lateral (i.e., width) dimensions of the scanned object (e.g., patient size) based on the scanogram obtained in step 404.

In step 406a, the processing circuitry calculates a modulation transfer function (MTF) based on information obtained in steps 403a and 405.

The MTF (f, mA) is a non-linear function of the determined scanning and reconstruction parameters, the X-ray tube currents, the patient dimensions and local HU variations of the object. Noted that f is a spatial frequency, which can be represented as line pairs per millimeter (lp/mm).

A look-up table (LUT) approach can be used to obtain the MTF(f, mA). The look-up table includes a plurality of scanning and reconstruction parameters, such as the X-ray tube currents mA, patient dimensions, and HU variations of the object.

A raw data simulation approach can also be used to obtain the value of MTF(f,mA). At first, in this method, simulation data is prepared with only two cylindrical objects. One cylindrical object is used to simulate the patient dimension obtained from the scanogram. The other cylindrical object is a task object, defined as a simulated test signal, from which an MTF can be measured, of the desired size, contrast, and position that is pre-defined by a user. The background noise is determined by the patient size and the X-ray tube current mA. Then, reconstruction is performed on the simulation data. Finally, a contrast-dependent MTF is measured from the reconstructed data based on the location of the object.

In step 406b, the processing circuitry calculates an object function (OBJ) based on information obtained in step 403b.

Figure 5A:
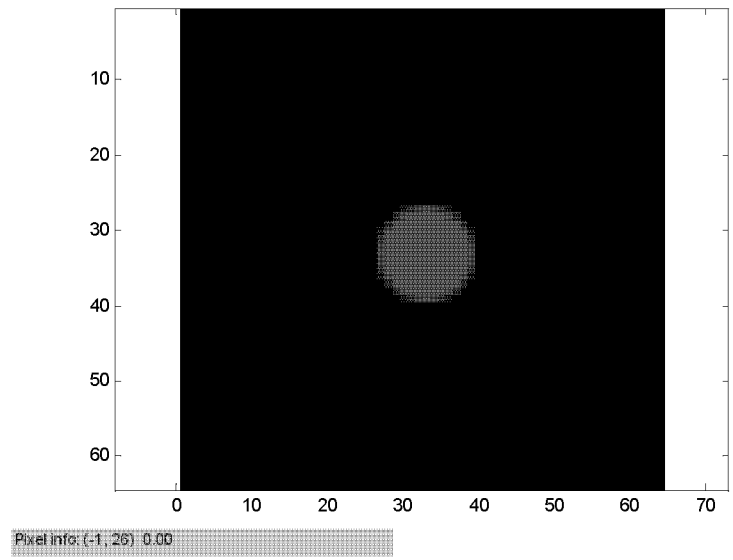
FIGS. 5A-B illustrate exemplary graphs of phantom with different tasks.
Figure 5B:
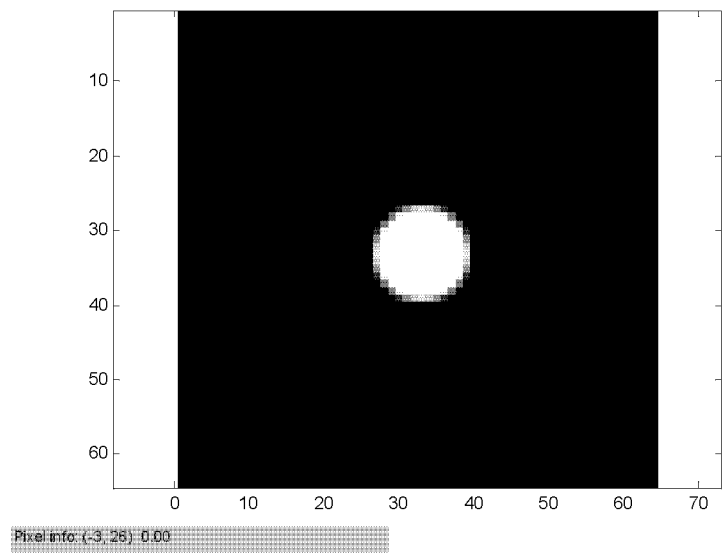

Obj(f) is a function of the size and attenuation of the object of interest being scanned and can be chosen based on the type of scan. The dimension and the HU contrast are related to the particular imaging task, or the purpose of the scan. For example, FIG. 5A illustrates a screening of a lesion in the liver with iodine, which has a diameter of 5 mm and an HU contrast on the order of 50 HU. FIG. 6B illustrates lung screening, which has a diameter of 2 mm and an HU contrast of 300 HU.

In step 406c, the processing circuitry calculates a noise power spectrum (NPS) function based on information obtained in steps 403a and 405.

NPS(f) is a function of the scanning and reconstruction parameters, which includes the nonlinear algorithms, the X-ray tube currents, and the patient size. The value of NPS can be obtained using the same approach as with MTF, i.e., either the LUT approach or the simulation approach can be used to obtain the NPS value.

In step 406d, the processing circuitry calculates an eye filter E(f), which is an known empirical equation In step 408, the processing circuitry determines the X-ray tube current mA by searching for an mA value that achieves a pre-defined optimal detectability index based on Equation (1) below. The pre-defined detectability index can be specified by qualitatively, e.g., by using terms such as "HQ" (i.e., High Quality), "STD" (i.e., Standard), and "lowdose". For example, d'(HQ)=6.0, d'(STD)=5.6, and d'(LowDose)=5.2, where $$d' = \frac{\int\int MTF(f)^2 Obj(f)^2 df_x df_y}{\int\int NPS(f) df_x df_y} \qquad (1)$$

and $df_x$ and $df_y$ refer to variables of integration, namely the x and y frequency space dimensions.

In step 410, the processing circuitry causes the X-ray source to perform a CT scan using the determined X-ray tube current. The processing circuitry uses the determined X-ray tube current to acquire data, reconstruct an image using the acquired data, and then display the reconstructed image.

The disclosed embodiments can be used with adaptive processing such as a hybrid image filter, or a true image filter. The X-ray tube current can be determined by the desired detectability index of the task. The image quality and/or the X-ray tube current can be changed by changing the desired detectability index. Since MTF(f), Obj(f), and NPS(f) include not only mA, but also kVp, the disclosed embodiments can be used to obtain the optimal kVp and mA.

Figure 6A:
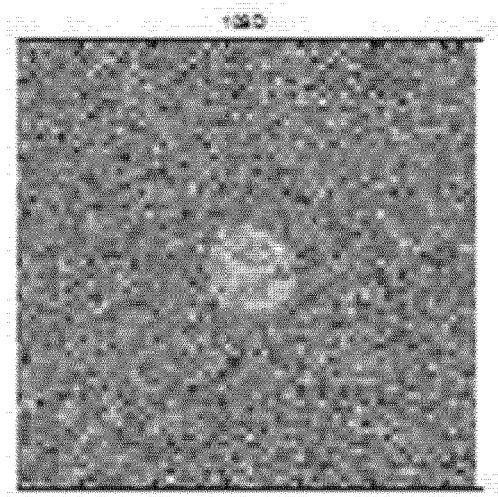
FIGS. 6A-C illustrate exemplary graphs of phantoms with various detectability indexes and noise standard deviations.
Figure 6B:
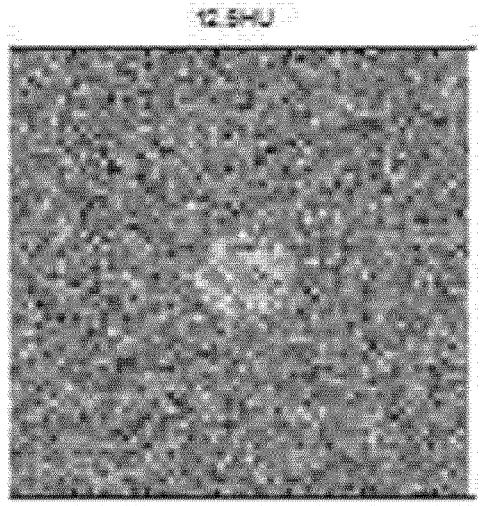
Figure 6C:
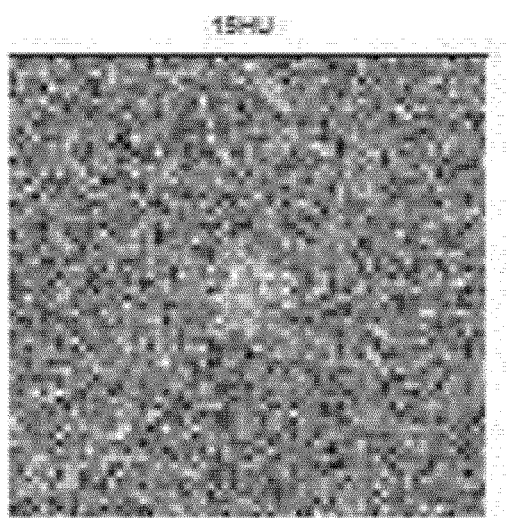

FIG. 6A shows a phantom with a detectability of 6.0 and a SD of 10 HU, while FIG. 6B shows a phantom with a detectability of 5.6 and a SD of 12.5 HU. FIG. 6C shows a phantom with a detectability of 5.2 and a SD of 15 HU. Thus, FIGS. 6A-6C illustrate that the detectability index decreases as the noise standard deviation increases.

Figure 7:
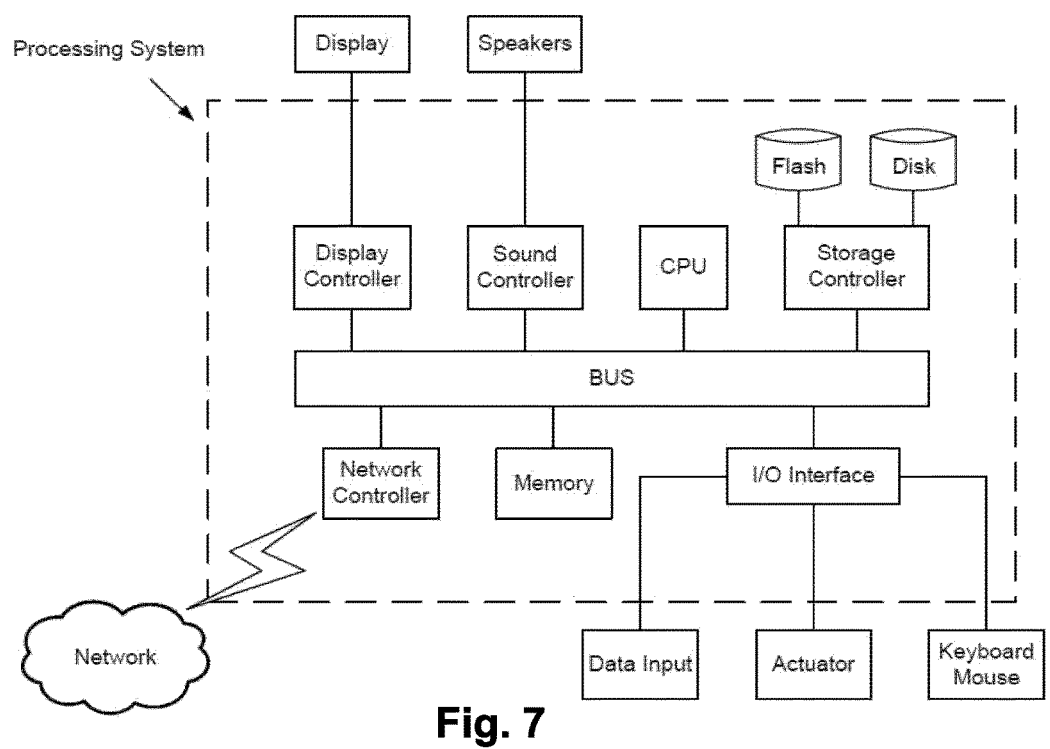
FIG. 7 illustrates a schematic diagram of an exemplary processing system.

An exemplary processing system is illustrated in FIG. 7, which is an exemplary implementation of the system controller 110 of FIG. 1. The system controller 110 can be a hardware device, e.g., a CPU that has been specifically configured to execute one or more computer programs that cause the CPU to perform the functions illustrated in the flowchart of FIG. 4. In particular, this exemplary controller can be implemented using one or more microprocessors or the equivalent, such as a central processing unit (CPU) and/or at least one application-specific processor ASP (not shown). A microprocessor is a circuit or circuitry that utilizes a computer readable storage medium, such as a memory circuit (e.g., ROM, EPROM, EEPROM, flash memory, static memory, DRAM, SDRAM, and their equivalents), configured to control the microprocessor to perform and/or control the processes and systems of this disclosure, and configured to execute the algorithms described herein. Other storage mediums can be controlled via a controller, such as a disk controller, which can controls a hard disk drive or optical disk drive.

The microprocessor or aspects thereof, in alternate implementations, can include or exclusively include a logic device for augmenting or fully implementing aspects of this disclosure. Such a logic device includes, but is not limited to, an application-specific integrated circuit (ASIC), a field programmable gate array (FPGA), a generic-array of logic (GAL), and their equivalents. The microprocessor can be a separate device or a single processing mechanism. Further, this disclosure can benefit from parallel processing capabilities of a multi-cored CPU and a graphics processing unit (GPU) to achieve improved computational efficiency. One or more processors in a multi-processing arrangement may also be employed to execute sequences of instructions contained in memory. Alternatively, hard-wired circuitry may be used in place of or in combination with software instructions. Thus, the exemplary implementations discussed herein are not limited to any specific combination of hardware circuitry and software.

In another aspect, results of processing in accordance with this disclosure can be displayed via a display controller to a monitor. The display controller preferably includes at least one graphic processing unit, which can be provided by a plurality of graphics processing cores, for improved computational efficiency. Additionally, an I/O (input/output) interface is provided for inputting signals and/or data from microphones, speakers, cameras, a mouse, a keyboard, a touch-based display or pad interface, etc., which can be connected to the I/O interface as a peripheral. For example, a keyboard or a pointing device for controlling parameters of the various processes or algorithms of this disclosure can be connected to the I/O interface to provide additional functionality and configuration options, or control display characteristics. Moreover, the monitor can be provided with a touch-sensitive interface for providing a command/instruction interface.

The above-noted components can be coupled to a network, such as the Internet or a local intranet, via a network interface for the transmission or reception of data, including controllable parameters. A central bus is provided to connect the above hardware components together and provides at least one path for digital communication there between.

The system controller 110 of FIG. 1 can be implemented utilizing one or more processing systems in accordance with the exemplary implementation shown in FIG. 7. In particular, one or more circuits or computer hardware units coinciding with one or more of the devices illustrated in FIG. 1 can provide for the functions of the system controller 110 (collectively or separately). The functional processing described herein can also be implemented in specialized circuitry or one or more specialized circuits including circuits to perform the described processing. Such circuits can be a part of a computer processing system or a discrete device that is interconnected to other systems. A processing circuitry in accordance with this disclosure can also be programmed to or configured to execute the functional processing described herein by computer code elements.

Further, the processing systems, in one implementation, can be connected to each other by a network or other data communication connection. One or more of the processing systems can be connected to corresponding actuators to actuate and control movement of the gantry, the X-ray source, and/or the patient bed.

Suitable software can be tangibly stored on a computer readable medium of a processing system, including the memory and storage devices. Other examples of computer readable media are compact discs, hard disks, floppy disks, tape, magneto-optical disks, PROMs (EPROM, EEPROM, flash EPROM), DRAM, SRAM, SDRAM, or any other magnetic medium, compact discs (e.g., CD-ROM), or any other medium from which a computer can read. The software may include, but is not limited to, device drivers, operating systems, development tools, applications software, and/or a graphical user interface.

Computer code elements on the above-noted medium may be any interpretable or executable code mechanism, including but not limited to scripts, interpretable programs, dynamic link libraries (DLLs), Java classes and complete executable programs. Moreover, parts of the processing of aspects of this disclosure may be distributed for better performance, reliability and/or cost.

The data input portion of the processing system accepts input signals from a detector or an array of detectors by, e.g., respective wired connections. A plurality of ASICs or other data processing components can be provided as forming the Data Input portion, or as providing input(s) to the data input portion. The ASICs can receive signals from, respectively, discrete detector arrays or segments (discrete portions) thereof. When an output signal from a detector is an analog signal, a filter circuit can be provided, together with an analog-to-digital converter for data recording and processing uses. Filtering can also be provided by digital filtering, without a discrete filter circuit for an analog signal. Alternatively, when the detector outputs a digital signal, digital filtering and/or data processing can be performed directly from the output of the detector.

While certain implementations have been described, these implementations have been presented by way of example only, and are not intended to limit the scope of this disclosure. The novel devices, systems and methods described herein may be embodied in a variety of other forms; furthermore, various omissions, substitutions, and changes in the form of the devices, systems and methods described herein may be made without departing from the spirit of this disclosure. The accompanying claims and their equivalents are intended to cover.

The invention claimed is:

1. A computed tomography (CT) apparatus, comprising:
an X-ray source to emit X-rays; and
processing circuitry configured to
receive a desired detectability index set by a user, the desired detectability index determining a desired image quality of a CT scan of an object;
determine an X-ray tube current that will result in the desired detectability index set by the user; and
cause the X-ray source to perform a scan of the object using the determined tube current,
wherein the desired detectability index is proportional to a module transfer function and an object function, and is inversely proportional to a noise power spectrum, and wherein the processing circuitry is further configured to calculate the module transfer function based on dimensions of the object, an input tube current, a contrast value, and scanning and reconstruction parameters.

2. A computed tomography (CT) imaging method for a CT apparatus that includes an X-ray source configured to emit X-rays, comprising:
receiving a desired detectability index set by a user for a desired image quality of a CT scan of an object;
determining an X-ray tube current that will result in the desired detectability index set by the user; and
causing the X-ray source to perform a scan of the object using the determined tube current,
wherein the desired detectability index is proportional to a module transfer function and an object function, and is inversely proportional to a noise power spectrum, and wherein determining the X-ray tube current further comprises calculating the module transfer function based on dimensions of the object, an input tube current, a contrast value, and scanning and reconstruction parameters.

3. A non-transitory computer-readable medium storing executable instructions, which, when executed by processing circuitry of a CT apparatus that includes an X-ray source configured to emit X-rays, cause the processing circuitry to execute a method comprising:
receiving a desired detectability index set by a user for a desired image quality of a CT scan of an object;
determining an X-ray tube current that will result in the desired detectability index set by the user; and
causing the X-ray source to perform a scan of the object using the determined tube current,
wherein the desired detectability index is proportional to a module transfer function and an object function, and is inversely proportional to a noise power spectrum, and wherein determining the X-ray tube current further comprises calculating the module transfer function based on dimensions of the object, an input tube current, a contrast value, and scanning and reconstruction parameters.

4. A computed tomography (CT) apparatus, comprising:
an X-ray source to emit X-rays; and
processing circuitry configured to
receive a desired detectability index set by a user, the desired detectability index determining a desired image quality of a CT scan of an object;

determine an X-ray tube current that will result in the desired detectability index set by the user; and cause the X-ray source to perform a scan of the object using the determined tube current, wherein the desired detectability index is proportional to a module transfer function and an object function, and is inversely proportional to a noise power spectrum, and wherein the processing circuitry is further configured to calculate the object function by determining a diameter and a contrast value from an image of the object.

5. A computed tomography (CT) imaging method for a CT apparatus that includes an X-ray source configured to emit X-rays, comprising:

receiving a desired detectability index set by a user for a desired image quality of a CT scan of an object;

determining an X-ray tube current that will result in the desired detectability index set by the user; and causing the X-ray source to perform a scan of the object using the determined tube current, wherein the desired detectability index is proportional to a module transfer function and an object function, and is inversely proportional to a noise power spectrum, and wherein determining the X-ray tube current further comprises calculating the object function by determining a diameter and a contrast value from an image of the object.

6. A non-transitory computer-readable medium storing executable instructions, which, when executed by processing circuitry of a CT apparatus that includes an X-ray source configured to emit X-rays, cause the processing circuitry to execute a method comprising:

receiving a desired detectability index set by a user for a desired image quality of a CT scan of an object;

determining an X-ray tube current that will result in the desired detectability index set by the user; and causing the X-ray source to perform a scan of the object using the determined tube current, wherein the desired detectability index is proportional to a module transfer function and an object function, and is inversely proportional to a noise power spectrum, and wherein determining the X-ray tube current further comprises calculating the object function by determining a diameter and a contrast value from an image of the object.

* * * * *